United States Patent
Endo et al.

(10) Patent No.: US 9,001,333 B2
(45) Date of Patent: Apr. 7, 2015

(54) RECORDING MEDIUM DETERMINING DEVICE AND RECORDING MEDIUM DETERMINATION METHOD

(71) Applicant: Seiko Epson Corporation, Tokyo (JP)

(72) Inventors: Tsunenobu Endo, Matsumoto (JP); Yuto Togawa, Matsumoto (JP); Shogo Kurosawa, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/148,428

(22) Filed: Jan. 6, 2014

(65) Prior Publication Data

US 2014/0192361 A1 Jul. 10, 2014

(30) Foreign Application Priority Data

Jan. 7, 2013 (JP) ................................. 2013-000371
Dec. 26, 2013 (JP) ................................. 2013-268710

(51) Int. Cl.
*G01N 21/55* (2014.01)
*G01N 21/47* (2006.01)
*G01N 21/31* (2006.01)
*G07D 7/12* (2006.01)

(52) U.S. Cl.
CPC ............ *G01N 21/4738* (2013.01); *G01N 21/31* (2013.01); *G01N 21/55* (2013.01); *G07D 7/122* (2013.01)

(58) Field of Classification Search
CPC ........ G01N 21/31; G01N 21/55; G07D 7/122
USPC .................................... 356/243.1, 243.4, 446
See application file for complete search history.

(56) References Cited

U.S. PATENT DOCUMENTS

| | | | | |
|---|---|---|---|---|
| 5,956,133 | A * | 9/1999 | Imura | 356/236 |
| 7,798,634 | B2 * | 9/2010 | Miyahara et al. | 347/106 |
| 2003/0197866 | A1 | 10/2003 | Uemura et al. | |
| 2005/0047299 | A1 | 3/2005 | Kikuchi et al. | |
| 2005/0219305 | A1 | 10/2005 | Kikuchi et al. | |
| 2007/0104071 | A1* | 5/2007 | Asoma | 369/112.05 |

FOREIGN PATENT DOCUMENTS

| | | |
|---|---|---|
| JP | 07-097099 | 4/1995 |
| JP | 07-234610 | 9/1995 |
| JP | 08-314327 | 11/1996 |
| JP | 09-114267 | 5/1997 |

(Continued)

*Primary Examiner* — Roy M Punnoose
(74) *Attorney, Agent, or Firm* — Workman Nydegger

(57) ABSTRACT

A recording medium determining device includes a light irradiating portion that irradiates a recording medium with visible light; a regular reflection light receiving portion that receives regular reflection light regularly reflected by the recording medium irradiated with light from the light irradiating portion; a diffused reflection light receiving portion that receives diffused reflection light diffusely reflected by the recording medium irradiated with light from the light irradiating portion; and a determining portion that determines the type of recording medium on the basis of each light amount of two or more visible light components with different wavelengths to one another among the light components received by the regular reflection light receiving portion and each light amount of two or more visible light components with different wavelengths to one another among the light components received by the diffused reflection light receiving portion.

8 Claims, 11 Drawing Sheets

(56) References Cited

FOREIGN PATENT DOCUMENTS

| | | |
|---|---|---|
| JP | 10-198093 | 7/1998 |
| JP | 2000-001002 | 1/2000 |
| JP | 2003-315260 | 11/2003 |
| JP | 2005-075469 | 3/2005 |
| JP | 2005-529313 | 9/2005 |
| JP | 2005-315856 | 11/2005 |
| JP | 2005315856 A * | 11/2005 |
| JP | 2006-058261 | 3/2006 |
| JP | 2007-033069 | 2/2007 |
| JP | 2007-057892 | 3/2007 |
| JP | 2008-020295 | 1/2008 |
| WO | 03/086771 | 10/2003 |

* cited by examiner

FIG. 6

|   | DIFFUSED REFLECTION LIGHT | REGULAR REFLECTION LIGHT |
|---|---|---|
| 1 | R, G, B | R, G, B |
| 2 | R, G, B | R, B |
| 3 | R, G | R, B |
| 4 | R, B | G, B |
| 5 | G, B | R, B |
| 6 | G, B | G, B |
| 7 | R, G | G, B |

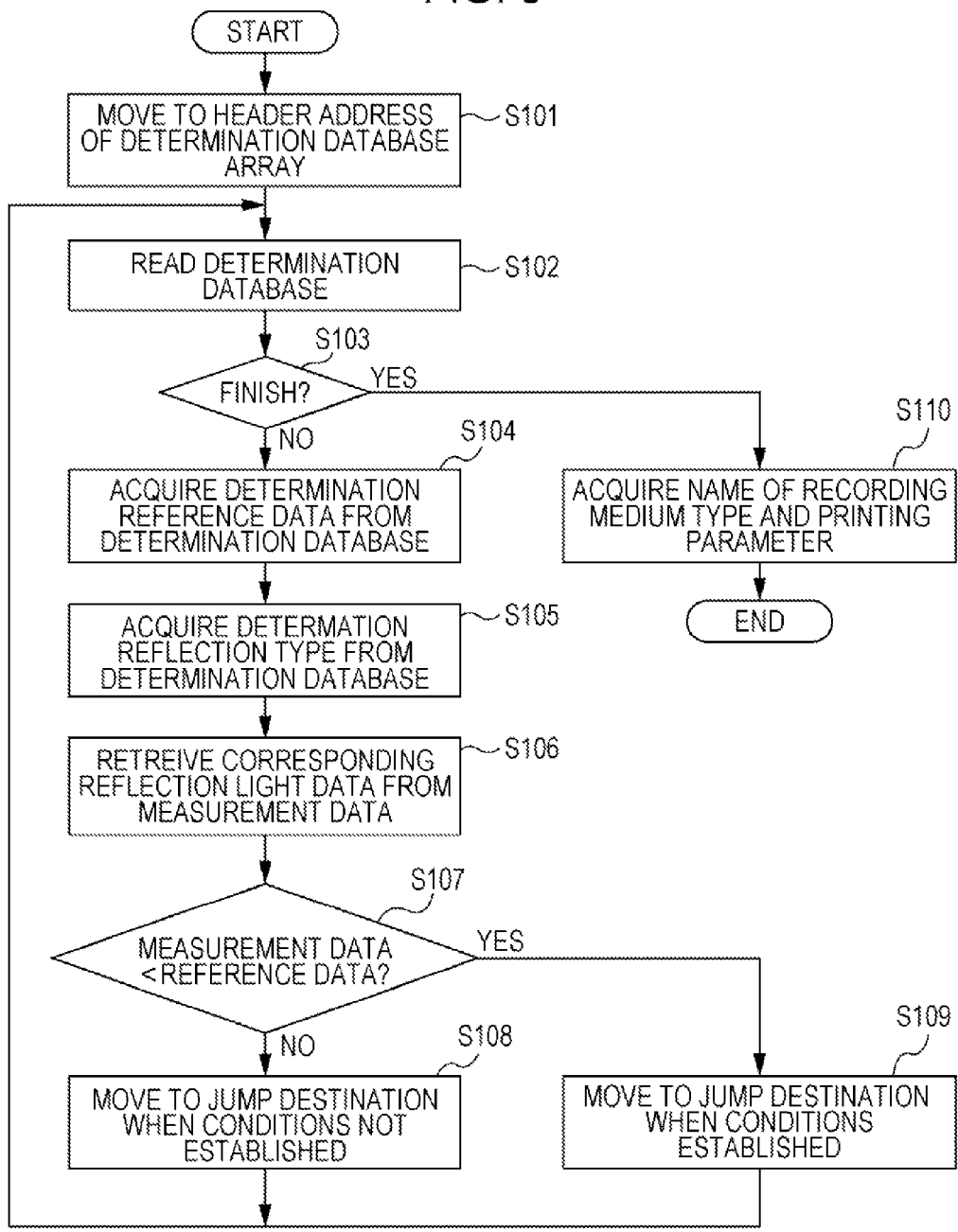

RECORDING MEDIUM DETERMINING DEVICE AND RECORDING MEDIUM DETERMINATION METHOD

BACKGROUND

1. Technical Field

The present invention relates to a recording medium determining device and a recording medium determination method that determine, for example, the type of recording medium such as paper, on which an image is recorded.

2. Related Art

In technologies that record an image on a recording medium such as paper or a resin sheet, there are cases where it is necessary to determine the type of recording medium used in order to optimize the recording conditions or a transport form according to, for example, the characteristics of the recording medium. There are technologies able to be used to this end which use the optical characteristics of the recording medium such as disclosed in JP-A-08-314327 and JP-A-2005-315856.

In the technology of the disclosure in JP-A-08-314327, the type of recording medium is determined on the basis of the intensity ratio of the regular reflection light and diffused reflection light received by a light receiving element along with light from an LED that is a light emitting element being made incident with respect to a recording medium. In the technology of the disclosure in JP-A-2005-315856, the type of recording medium is determined on the basis of each light amount of regular reflection light and diffused reflection light when the medium is irradiated with infrared light, and the light amount of a fluorescent component emitted from the recording medium when the medium is irradiated with ultraviolet light.

As types of recording media, there are numerous types in circulation in the market. Therefore, there is demand for accurately determining the type thereof; however, the technologies of the related art are unable to respond to such demand. For example, in the technology of the disclosure in JP-A-08-314327, because the determination is simply performed only with the intensity ratio of the regular reflection light and the diffused reflection light, a plurality of recording media with similar characteristics on this point are unable to be determined. In addition, in the technology of the disclosure in JP-A-2005-315856, although the reflection characteristics with respect to infrared light and the fluorescence characteristics with respect to ultraviolet light are taken as a determination reference, according to the findings described later of the inventors of the present application, the difference between the reflection characteristics of various recording media with respect to infrared light is extremely small, furthermore, the fluorescence with respect to ultraviolet light is mainly due to a brightening agent, and determination of the type of recording medium not including a brightening agent is unable to be made.

SUMMARY

An advantage of some aspects of the invention is to provide a technology able to more accurately determine various types of recording media.

According to an aspect of the invention, there is provided a recording medium determining device including a light irradiating portion that irradiates a recording medium with visible light; a regular reflection light receiving portion that receives regular reflection light regularly reflected by the recording medium irradiated with light from the light irradiating portion; a diffused reflection light receiving portion that receives diffused reflection light diffusely reflected by the recording medium irradiated with light from the light irradiating portion; and a determining portion that determines the type of recording medium on the basis of each light amount of two or more visible light components with different wavelengths to one another among the light components received by the regular reflection light receiving portion and each light amount of two or more visible light components with different wavelengths to one another among the light components received by the diffused reflection light receiving portion.

According to another aspect of the invention, there is provided a recording medium determination method, including irradiating a recording medium with visible light; receiving regular reflection light in which irradiated light is regularly reflected by the recording medium; receiving diffused reflection light in which irradiated light is diffusely reflected by the recording medium; and determining the type of recording medium on the basis of each light amount of two or more visible light components with wavelengths different to one another among the light components received in receiving the regular reflection light, and each light amount of two or more visible light components with wavelengths different to one another among the light components received in receiving the diffused reflection light.

According to the aspects of the invention, the type of recording medium is determined on the basis of the light amount of each of two or more visible light components among the regular reflection light and the diffused reflection light from the recording medium. Moreover, according to the aspects of the invention, although the determination may be performed using two or more light components from each of the regular reflection light and the diffused reflection light, the light component used in the regular reflection light and the light component used in the diffused reflection light may be the same or may be different.

Although described in detail later, according to new findings by the inventors of the present application, the reflection characteristics with respect to incident light for each type of recording medium vary more greatly in the visible region than in the infrared region, and further, the wavelength dependence of the reflection characteristics in the visible region differ greatly according to the type of recording medium. Using this, according to the aspects of the invention, determination of the recording medium is performed using the light amount of two or more wavelengths in each of regular reflection light and diffused reflection light. Therefore, it is possible to determine numerous types of recording medium with higher accuracy than in the related art.

According to the aspects of the invention, for example, the recording medium is preferably irradiated with light not substantially including ultraviolet rays. According to the aspects of the invention, since the type of recording medium is determined on the basis of the characteristics of regular reflection and diffused reflection of visible light incident on the recording medium, detection errors of the light amount due to mixed incidence of light components occurring due to fluorescence may be reduced by light not substantially including ultraviolet rays being made incident.

In addition, at least one of the visible light components of the diffused reflection light used in the determination, for example, may be a wavelength that corresponds to blue or green. In addition, at least one of the visible light components of the regular reflection light used in the determination may be a wavelength component that corresponds to blue. According to the findings of the inventors of the present application, the variance in reflection characteristics for each type of recording medium, for example, is more remarkable in the short wavelength components such as blue or green than in the long wavelength components such as red. Accordingly, it is possible to determine the type of recording medium with higher accuracy by using the short wavelength components in the determination.

In addition, according to the aspects of the invention, the recording medium is irradiated with light including two or more visible light components with wavelengths different to one another, and the light amount of each light component may be obtained by separating each of the regular reflection light and the diffused reflection light. By doing so, reflection light of each light component may be received at the same time, and the determination process may be performed in a short time. In order to achieve the advantage, for example, the light which the recording medium is irradiated with is set to white light, and a light receiving element provided with an RGB color filter that separates incident light into each of the R (red), G (green) and B (blue) components may be used.

Alternatively, for example, the recording medium is preferably irradiated by switching between two or more types of visible light with spectral distributions different to one another. In this case, regular reflection light and diffused reflection light are received by a light receiving element not having a color separation function, and the actions and effects according to the aspects of the invention may be obtained. In addition, it becomes easy to individually set the intensity of incident light for each light component, and it is possible to improve detection precision by expanding the dynamic range in the light amount detection.

In addition, the ratio of the light amount of regular reflection light from the recording medium and the light amount of regular reflection light from a predetermined reference reflection portion, and the ratio of the light amount of diffused reflection light from the recording medium and the light amount of diffused reflection light from a predetermined reference reflection portion is preferably obtained. In so doing, the reflectivity (described in detail later) which is the ratio of the reflected light from the reference reflection portion and the reflection light from the recording medium may be obtained. Therefore, even in a case in which there are variations in the characteristics of the light irradiating portion that irradiates a recording medium with light and the light receiving portion that receives reflection light, it is possible to stably perform determination according to determination in light of the reflectivity.

BRIEF DESCRIPTION OF THE DRAWINGS

The invention will be described with reference to the accompanying drawings, wherein like numbers reference like elements.

FIG. 6 is a diagram showing a combination of wavelength components for which the recording medium is determinable.

FIG. 8 is a flowchart showing one example of a recording medium determination process that is executed by the controller.

DESCRIPTION OF EXEMPLARY EMBODIMENTS

Initially, the findings of the inventors of the present application that are the basis of the aspects of the invention and the principles of the aspects of the invention of the present application based thereupon will be described. The inventors of the present application researched the spectral distribution of regular reflection light and diffused reflection light when a recording medium is irradiated with light for numerous types of recording medium in circulation in the market. Since while the regular reflection light that is light reflected by the surface of the recording medium reflects the state of the surface of the recording medium, diffused reflection light is light that is emitted again by being scattered in the interior of the recording medium, the characteristics of the material of the recording medium are better reflected.

Figure 1:
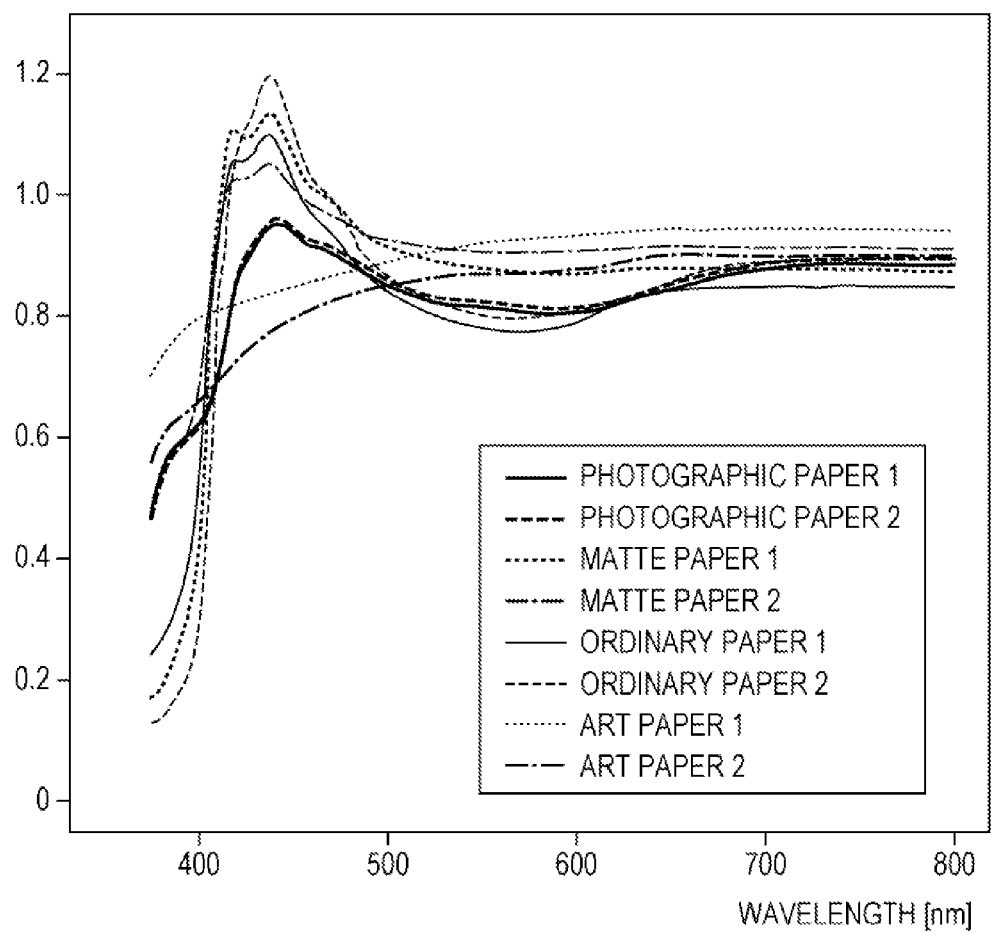
FIG. 1 is a diagram showing the spectral distribution of diffused reflection light in various recording media.

FIG. 1 is a diagram showing the spectral distribution of diffused reflection light in various recording media. In more detail, FIG. 1 is a diagram showing an example of a portion of the results of measuring the spectral distribution of light diffusely reflected by the recording medium when various recording media are irradiated with white light from a tungsten light source. Moreover, in FIG. 1, the ratio of the reflected light amount from the recording medium and the reflected light amount from a reference plate when irradiation light is made incident on a predetermined white reference plate is denoted as "reflectivity". Accordingly, in a material with a higher reflectiveness than the reference plate, there are cases where the reflectivity exceeds 1. Variations occur in the light amount received and identified by light receiving portion from the light irradiated by the irradiating portion according to the irradiation amount of the irradiating portion, the light receiving conditions of the light receiving portion, and the like. Therefore, by obtaining the ratio between the time in which the light amount of reflection light from the recording medium is obtained and the light amount of reflection light obtained from the reference plate in the same conditions in which the irradiation portion and the light receiving portion are combined, it is possible to stably confirm the reflection state of the recording medium.

Figure 3A:
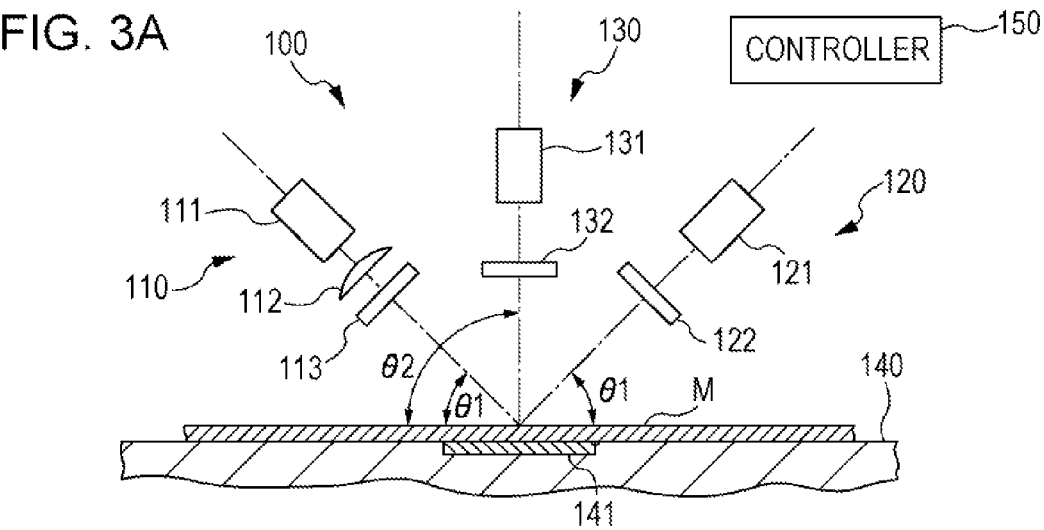
FIGS. 3A to 3C are diagrams showing one example of a specific configuration of a determining device according to an aspect of the invention.
Figure 3B:
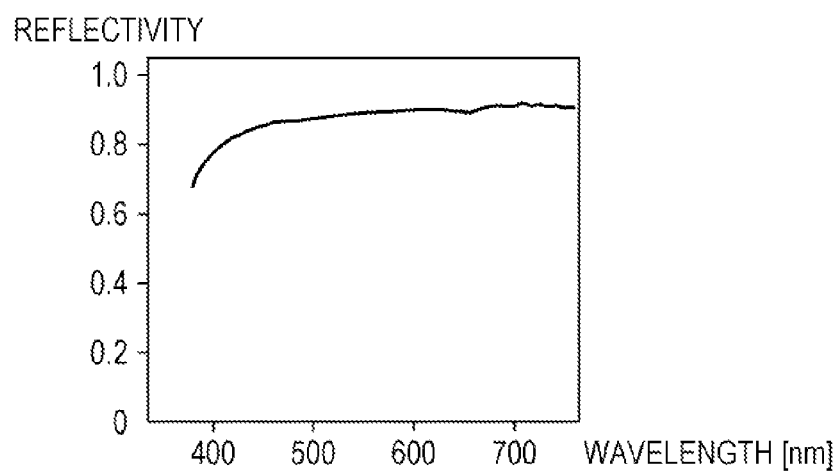
Figure 3C:
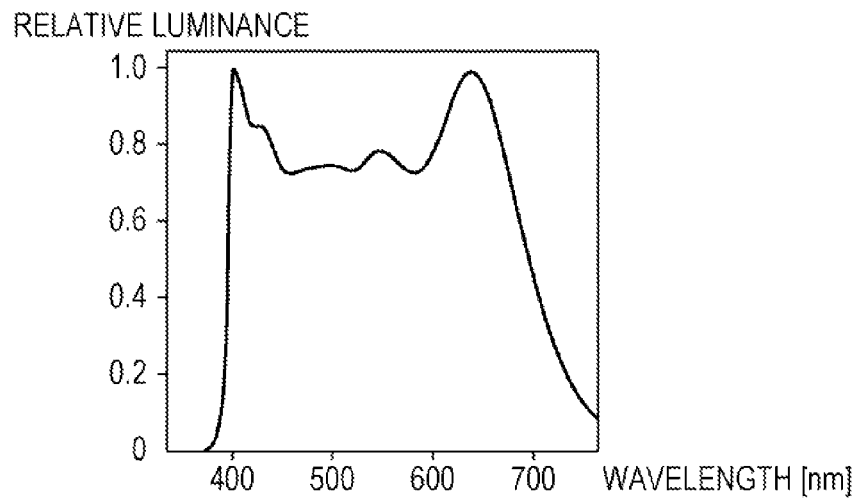

The irradiation light is white light from a tungsten light source which includes almost no components from a wavelength of 370 nm or lower to a wavelength of 400 nm or lower, or, as shown in FIG. 3C described later, is white light with high color rendering properties having a peak in each of the short wavelength side and the long wavelength side while substantially evenly including a visible region including almost no components with a wavelength of 400 nm or less and a wavelength of 700 nm or more (generally, a wavelength range of from 400 nm to 750 nm). The inventors of the present application obtained the following findings by performing spectrometry of the diffused reflective light by such light being made incident on the recording medium.

That is, as shown in FIG. 1, there is wavelength dependence in the reflectivity of the diffused reflection due to the recording medium and the value of the reflectivity in each wavelength differs greatly according to the type of recording medium. In particular, while each recording medium shows characteristic reflectivity in the short wavelength region of generally a wavelength from 400 nm to 500 nm, and the medium wavelength region of generally a wavelength from 500 nm to 600 nm, the variance in reflectivity for each recording medium is comparatively small in the long wavelength region of generally a wavelength of 600 nm or higher.

From this, it is understood that rather than simply detecting the light amount of the overall diffused light, the reflection light amount is separately detected for each wavelength component, and by combining and evaluating the values thereof, there is a possibility of being able to more finely identify the differences in the reflection characteristics of the recording media caused by differences in the material than in the related art.

That is, by using the reflection light intensity of two or more wavelength components with different wavelengths to one another from among the diffused reflection light in which incident light is diffusely reflected by the recording medium, it is possible to determine numerous types of recording medium with higher accuracy than the related art. In this case, it is desirable that the incident light not include ultraviolet light components, and the reason therefor is as below.

Figure 2:
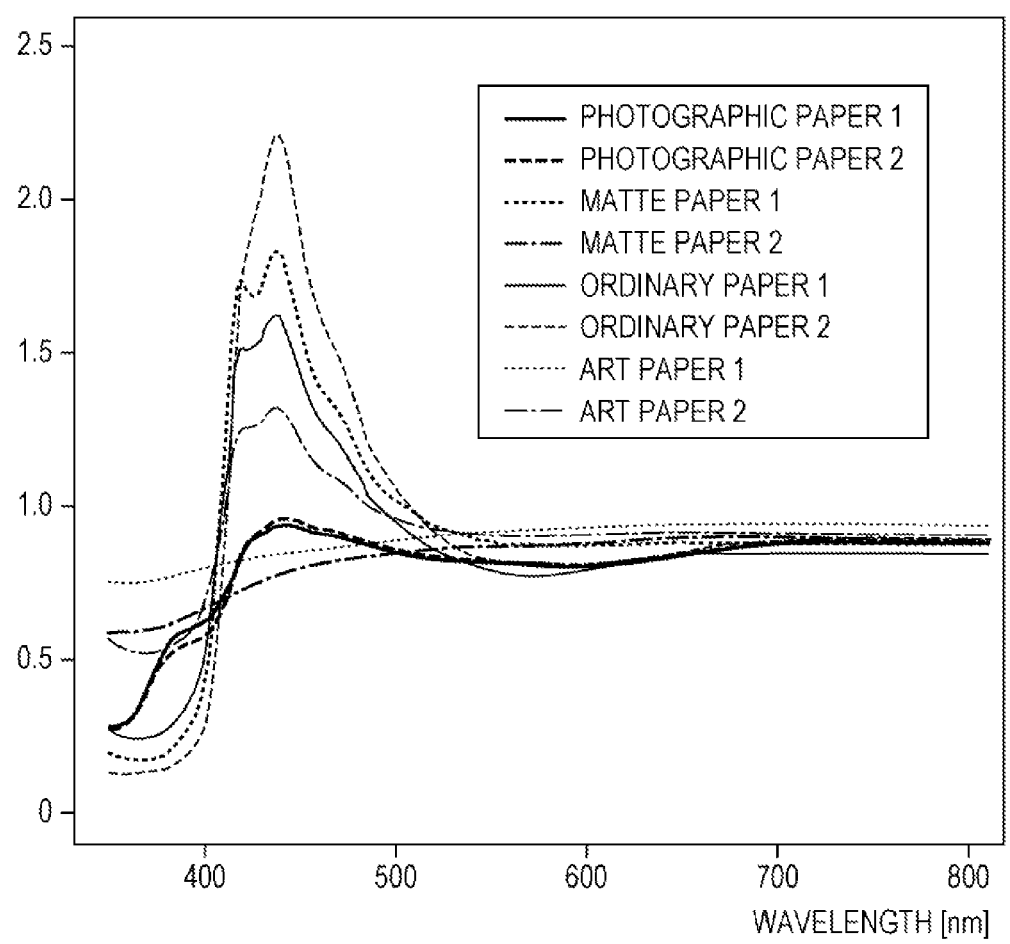
FIG. 2 is a diagram showing the spectral distribution of diffused reflection light when light including ultraviolet light is incident.

FIG. 2 is a diagram showing the spectral distribution of diffused reflection light when light including an ultraviolet light component is made incident on the recording medium. When light including an ultraviolet light component is incident on the recording medium, because fluorescent light excited by a fluorescent brightening agent included in the recording medium appears in the short wavelength region in addition to components in which the incident light is reflected, the apparent reflectivity in the short wavelength regions increases. Therefore, in a middle wavelength region and a long wavelength region, variance in the reflectivity caused by the type of recording medium becomes rather inconspicuous. Naturally, there is a little fluorescence excited by ultraviolet light in a recording medium not including a fluorescent brightening agent.

In this way, ultraviolet light components being included in the incident light, while emphasizing the variance for each recording medium in specified wavelength components, reduces the variance for each recording medium in other wavelength components. This becomes an obstruction in the technical conception of the aspects of the invention which is to determine the type of recording medium from the reflection light amount in two or more wavelengths. In addition, in the reflection light detected, the light components originally included in the incident light and the fluorescent light components excited by ultraviolet light are mixed in an indistinguishable state, and it is difficult to detect only the pure diffused reflection light component. The technical concept of the aspects of the invention is to specify the type of recording medium by ascertaining to what extent light components included in the incident light are reflected (regular reflection and diffused reflection) by the recording medium, and is not intended to detect light generated secondarily by the recording medium through light irradiation. From these reasons, it is desirable that the light incident on the recording medium not contain ultraviolet light components that excite fluorescent light. Naturally, it is permissible to include minute ultraviolet light components in a range that does not influence the measurement in the visible range.

As above, it is possible to determine the material of numerous recording media by detecting the light intensity of two or more wavelength components included in the diffused reflection light. Meanwhile, even if the materials of the base material of the recording media are the same, the type is distinguished through differences in the surface working, and it is possible for the differences in surface working to be determined by the light intensity of the regular reflection light.

Since the spectral distribution of regular reflection light is, in principle, substantially the same as the spectral distribution of incident light, it is possible to determine the surface state of a recording medium if the light intensity of specified wavelength components of the regular reflection light is able to be detected. That is, if the light intensity of two or more wavelength components included in the diffused reflection light and the light intensity of at least one wavelength component included in regular reflection light are obtained, it is possible in principle to specify the type of recording medium. However, in experiments by the inventors of the present application using dozens of types of recording media available on the market, it was determined that it is desirable to use the values of the reflection light intensity of two or more wavelength components for the regular reflection light in order to accurately determine these recording media. In other words, even in the reflection light intensity of regular reflection light, some wavelength dependence is visible.

Based on the findings, according to an aspect of the invention, the light intensity of two or more wavelength components for each of the regular reflection light and the diffused reflection light are separately obtained and determination of the type of recording medium is performed on the basis of the results thereof. More specifically, using the light intensity of each wavelength component thus obtained and a determination reference set on the basis of optical characteristics obtained in advance for a plurality of types of recording medium, it is determined to which of known recording media the recording medium that is a determination target corresponds. By doing so, it is possible to determine numerous types of recording medium with high accuracy.

FIGS. 3A to 3C are diagrams showing one example of a specific configuration of a determining device according to an aspect of the invention. The determining device 100 determines the type of recording medium by being mounted to various image recording apparatuses, such as a printing device, copy machine or printer. The printing method thereof is not particularly limited, and is applicable to various methods, such as a transfer method, an ink jet method, or an electrophotographic method.

In the determining device 100 in the configuration example shown in FIG. 3A, a light source device 110 is provided above a platen 140 in which a reference reflection plate 141 having predetermined reflection characteristics is embedded. It is desirable that the reference reflection plate 141, as shown by an example of reflection characteristics in FIG. 3B, be a material with a white surface having generally constant and comparatively high (for example, 0.75 or higher) reflectivity in the visible light region of 400 nm to approximately 750 nm. It is possible to use a sintered compact or a ceramic of a powder such as titanium nitride, barium sulfate or aluminum oxide, or a white plastic, for example, an aggregate or foamed material of a powder such as an acrylic resin or a polycarbonate resin as the reference plate having such reflection characteristics. Furthermore, the reference plate may have a coating layer such as glass on the surface thereof in order to prevent abrasion or fouling of the surface or to adjust the degree of gloss.

When "reflectivity" of a recording medium is used in the following description, the term is defined as the value of the ratio of the light amount of reflection light detected in the recording medium and the light amount of reflection light detected in advance in a reference reflection plate 141. The "reflectivity" of a recording medium thus defined is not easily influenced by variations in individual characteristics and changes over time in the light source and contributes to improvements in the determination precision. Moreover, it is desirable that a calibration in which reflection light from the reference reflection plate 141 is detected again be executed, as appropriate.

The light source device 110 includes a light source portion 111 that emits light having a predetermined spectral distribution and intensity, a light collecting portion 112 that collects emitted light from the light source portion 111, and a diaphragm portion 113 that regulates the radiation direction of the collected light. The light source device 110 irradiates light towards the reference reflection plate 141 on the platen 140 from diagonally above. The incidence angle θ1 on the reference reflection plate 141 of light from the light source device 110 is preferably 30 degrees to 60 degrees, and may be set to, for example, 45 degrees.

It is possible to use white light having the spectral distribution shown in FIG. 3C, for example, as the irradiation light herein, and it is possible to use a white LED, for example, as the light source portion 111. Although a discharge lamp such as a xenon arc lamp or an incandescent lamp such as a halogen lamp may be used as a light source, and in this case, in order for the ultraviolet light component to be reduced, it is desirable that a filter that removes the wavelength components of 380 nm or less, and more preferably 400 nm or less, be used.

A regular reflection light detecting device 120 is arranged on the optical path of light emitted from the light source device 110 and regularly reflected by the reference reflection plate 141. That is, the angle anticipated by the regular reflection light detecting device 120 for the reference reflection plate 141 is substantially equal to the incident angle θ1. The regular reflection light detecting device 120 receives regular reflection light from the reference reflection plate 141 and outputs a signal according to the received light amount.

Meanwhile, a diffused light detecting device 130 that receives diffused reflection light from the reference reflection plate 141 is provided at a position that anticipates the reference reflection plate 141 at an angle θ2 greater than the incident angle θ1. It is possible for the angle θ2 to be, for example, 90 degrees.

The regular reflection light detecting device 120 includes a light receiving portion 121 that outputs a signal according to the received light amount for each component in which light is received and separated into several wavelengths, and a diaphragm portion 122 that controls the direction of light incident on the light receiving portion 121. Similarly, the diffused light detecting device 130 includes a light receiving portion 131 and a diaphragm portion 132. It is possible for the regular reflection light detecting device 120 and the diffused light detecting device 130 to use the same configuration as one another.

Figure 4A:
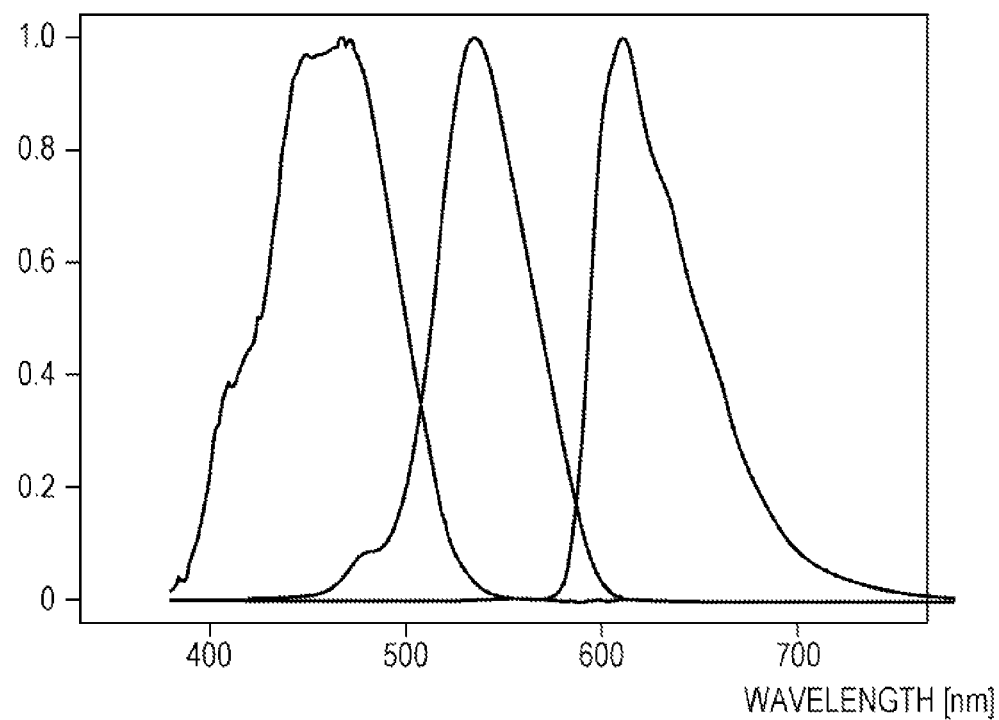
FIGS. 4A and 4B are diagrams showing an example of spectral sensitivity characteristics of a light receiving portion.
Figure 4B:
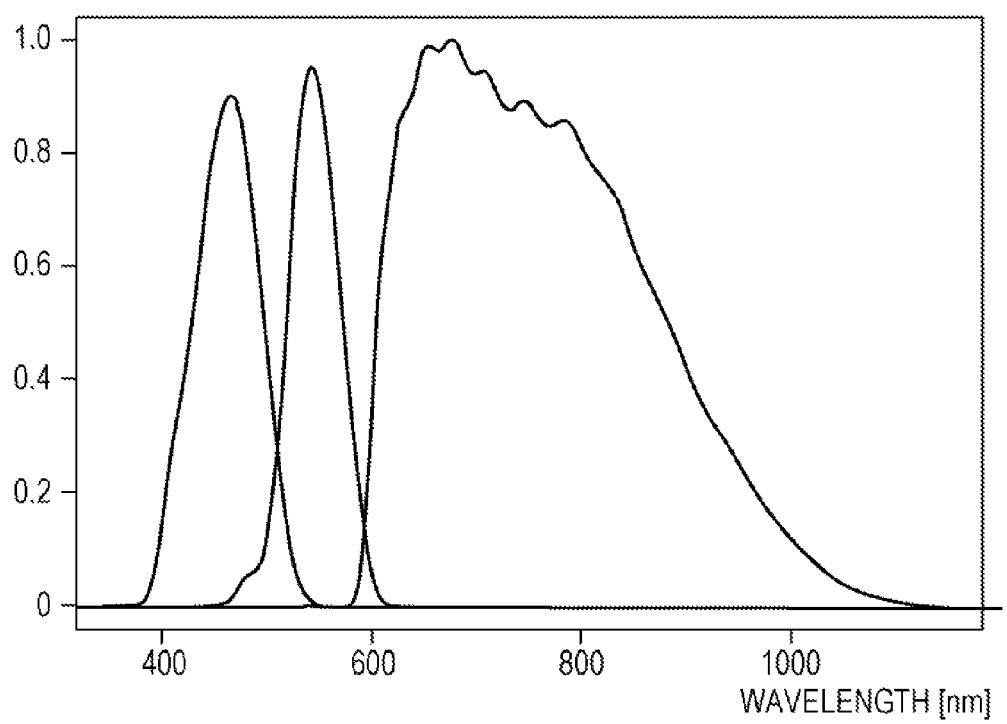

FIG. 4A is a diagram showing an example of spectral sensitivity characteristics of a light receiving portion. FIG. 4B is a diagram showing an example of spectral sensitivity characteristics of a light receiving portion. In the example in FIG. 4A, the incident light is separated into blue (B) component with a wavelength of 400 nm to approximately 540 nm (center wavelength 460 nm), a green (G) component with a wavelength of 480 nm to approximately 600 nm (center wavelength 540 nm), and a red (R) component with a wavelength of 590 nm to approximately 720 nm (center wavelength 620 nm to 660 nm). In addition, in the example in FIG. 4B, the spectral sensitivity of the R component is enlarged to the infrared region, and the bandwidth thereof is 590 nm to 1200 nm (center wavelength 620 nm to 720 nm). These are the representative characteristics of RGB color filters that are in practical use, and it is possible to use a general color CCD sensor or color CMOS sensor or the like as a light receiving portion having such spectral sensitivity characteristics. Therefore, it is possible to suppress the device costs to be low.

Description of the configuration of the determining device continues by returning to FIGS. 3A to 3C. In addition to each of the above configurations, a controller 150 that executes a determination process of a recording medium along with governing the operations thereof is provided in the determining device 100. In the determining device 100 configured as above, when a recording medium M that is the determination target is arranged on the platen 140, light is irradiated from the light source device 110, regular reflection light therefrom is received by the regular reflection light detecting device 120, whereas diffused reflection light is received by the diffused light detecting device 130. The regular reflection light detecting device 120 and the diffused light detecting device 130 separate received light into components of each of the RGB colors, and respectively output signals according to the received light amount for each component with respect to the controller 150.

The controller 150 determines the type of recording medium M on the basis of the value of the light amount of two or more wavelength components among each of the RGB components of the regular reflection light detected by the regular reflection light detecting device 120, and the value of the light amount of two or more wavelengths among each of the RGB color components of the diffused reflection light detected by the diffused light detecting device 130. Next, the recording medium determination process using the controller 150 will be described.

In the recording medium determination process using the controller 150, reflection data for regular reflection and diffused reflection is obtained in advance for each of the RGB color components for a plurality of types of recording medium that may be determination targets. Then, when the recording medium M to be determined is provided, the light amount of regular reflection light and diffused reflection light are detected for each of the RGB color components for the recording medium M, the detected values thereof are compared to those of known recording media, and it is determined that the recording medium with the closest characteristics and the recording medium M are the same type.

It is possible to perform various methods of comparing and contrasting the recording medium M that is the determination target and the known recording medium, and the characteristics of the recording medium M are preferably analyzed using learning data that is machine learned in light of reflection characteristic data of the known recording media, and the recording medium having characteristics close to the recording medium M is selected using a known multivariate analysis technique. Here, as a processing example applied to computer processing, description of an example of determination using a binary tree analysis structured on the basis of known reflection data.

Figure 5:
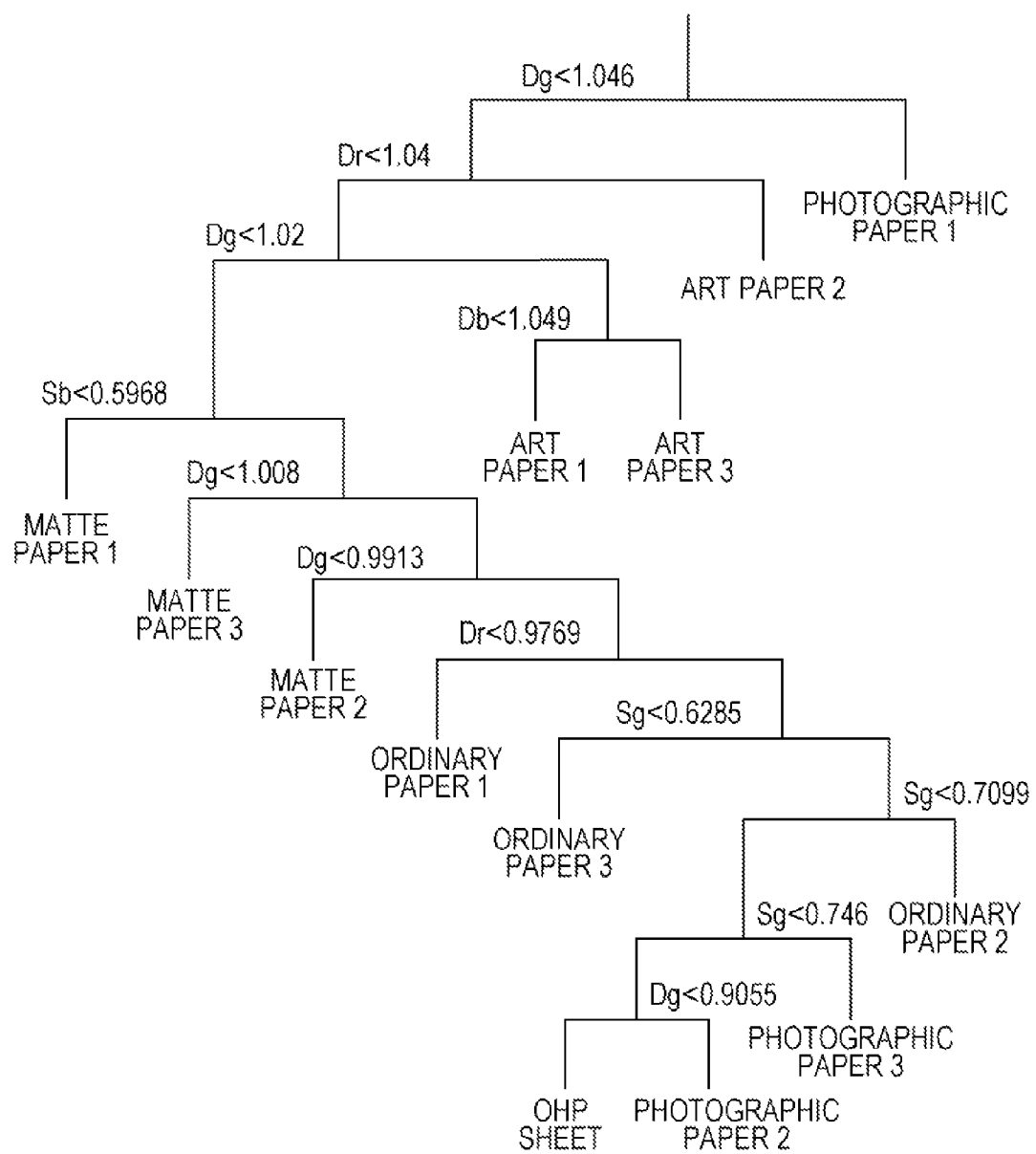
FIG. 5 is a diagram showing one example of a binary tree obtained from known reflection data.

FIG. 5 is a diagram showing one example of a binary tree obtained from known reflection data. In the example, thirteen types among the various commercially available recording media, specifically three types of ordinary paper (ordinary paper 1 to 3), three types of photographic paper (photographic paper 1 to 3), three types of art paper (art paper 1 to 3), three types of matte paper (matte paper 1 to 3) and one type of transparent OHP sheet for ink jet printing, were selected, and were structured in a binary tree for distinguishing each recording medium using reflectivity data for regular reflection and diffused reflection measured for each of the RGB color components in the media. Moreover, since methods of structuring a binary tree from sample data are known, description thereof will not be made here.

In the drawing, the references Sg and Sb indicate the value of the reflectivity of regular reflection light in the green (G) and blue (B) components respectively, and the references Dr and Dg indicate the values of the reflectivity of diffused reflection light in the red (R) and green (G) components respectively. In addition thereto, there is the reflectivity of the red component in regular reflection light and of the blue component in the diffused reflection light as the reflectivity data, and below these values are represented by the references Sr and Db respectively.

The reflectivity is obtained from the light amount of each component detected in the recording medium M that is a determination target, and it is possible to determine the type of the recording medium M by performing analysis using a structured binary tree. More specifically, at each node of the binary tree, one designated value from the obtained reflectivity data is selected and compared to the reference value, searching is performed towards the lower layer while selecting one child according to the magnitude relationship thereof. In so doing, any of the thirteen types of recording medium defined as "leaves" of the binary tree is finally arrived at and is set as the determination results. In the example, as a result of structuring the binary tree using reflectivity data obtained with each recording medium it is possible to more reliably determine the thirteen types of recording medium from the reflectivity Sg and Sb of the two color components of regular reflection light and the reflectivity Dr and Dg of the two color components of diffused reflection light.

In this way, not all of the reflectivity data for the three color components of each of the regular reflection light and the diffused reflection light are necessary at all times. In addition, the tree shape of the binary tree shown in FIG. 5, the type of reflection light component used in the analysis, and the numerical value of the reflectivity are considered to be naturally different according to the combination of recording media for which data is acquired in advance. However, according to the results of trials by the inventors of the present application performed while making various changes to the combination of reflectivity data that is applied to the process for around thirty types of commercially available recording medium, it was understood that the two or more wavelength components for regular reflection light and the two or more wavelength components for diffused reflection light are necessary for accurate determination. That is, the combination of the light intensity of a plurality of wavelength components in which the reflection light are different to one another differs according to the type of recording medium, and is necessary in order to determine the type of recording medium.

FIG. 6 is a diagram showing a combination of wavelength components for which the recording medium is determinable. As shown in the drawing, although it is natural that reliable determination is possible if all of the RGB components of each of the regular reflection light and the diffused reflection light are used, it is understood that reliable determination is possible even if only two color components are used from each of the regular reflection light and the diffused reflection light. From the results, it is understood that it is preferable that the blue component in the regular reflection light be used in determination, and further, preferable that blue and green components in the diffused reflection light be used, and furthermore, preferable that the blue component and green component be included together among the four types of the two regular reflection light components and the two diffused reflection light components.

In this way, when determining the type of recording medium by detecting regular reflection light and diffused reflection light of the visible light with which the recording medium is irradiated, it is possible to perform the determination with high accuracy by using the reflection light intensity of the blue component and green component with comparatively short wavelengths from the visible range. This is consistent with the variance in the reflection characteristics of each type of recording medium shown in FIG. 1, that is, the reflection light amount for each recording medium being small in the short wavelength band and comparatively large in the long wavelength band. Accordingly, it is desirable that the irradiation light include a large amount of components with short wavelengths to long wavelengths, that is the blue component and green component, from the visible range. However, since inclusion of a fluorescent light component excited by the ultraviolet light component included in the irradiation light is a cause of determination errors, it is desirable that the irradiation light be light not substantially including an ultraviolet light component or from which the ultraviolet light component is removed in advance. A white LED with high color rendering properties may be suitably used as a light source towards this advantage.

Moreover, as described above, determination of the type of recording medium is able to be performed on the basis of the light amount detection results of two or more wavelength components of each of the regular reflection light and diffused reflection light. Accordingly, separating the received reflection light into three components (RGB) is not a necessary condition. However, even in a case in which all three color components are not used in the determination, it is desirable that the device have a color separation function for the three colors. The first reason is that if the combination of the plurality of types of recording medium that is the determination target changes, there is a possibility for the color component used in the determination to also change. The second reason is that optical devices having a color separation function for the three colors are currently easily available, and there is a possibility of being able to suppress the device costs to be lower than preparing hardware for extracting only two wavelength components.

Figure 7A:
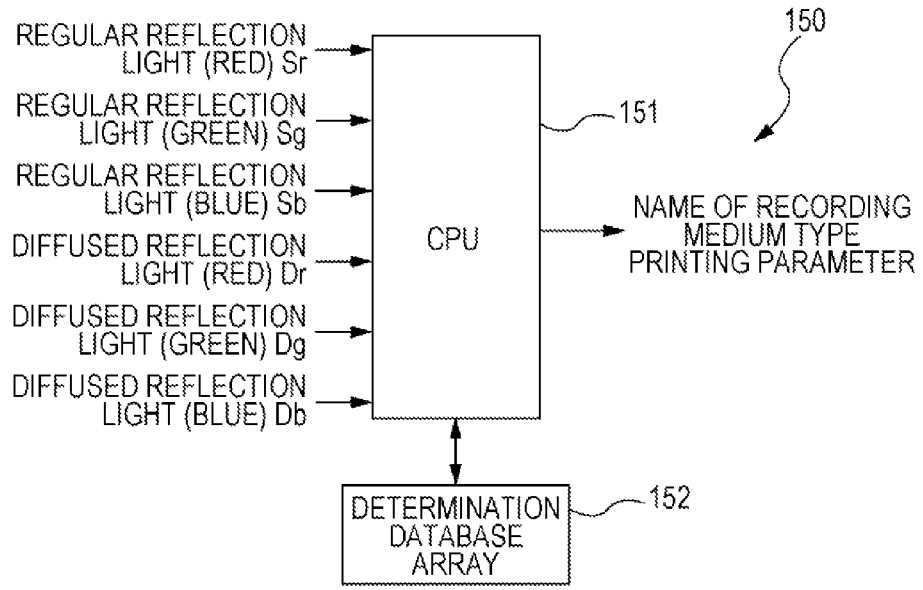
FIGS. 7A and 7B are diagrams schematically showing a configuration of a controller for performing a recording medium determination process.
Figure 7B:
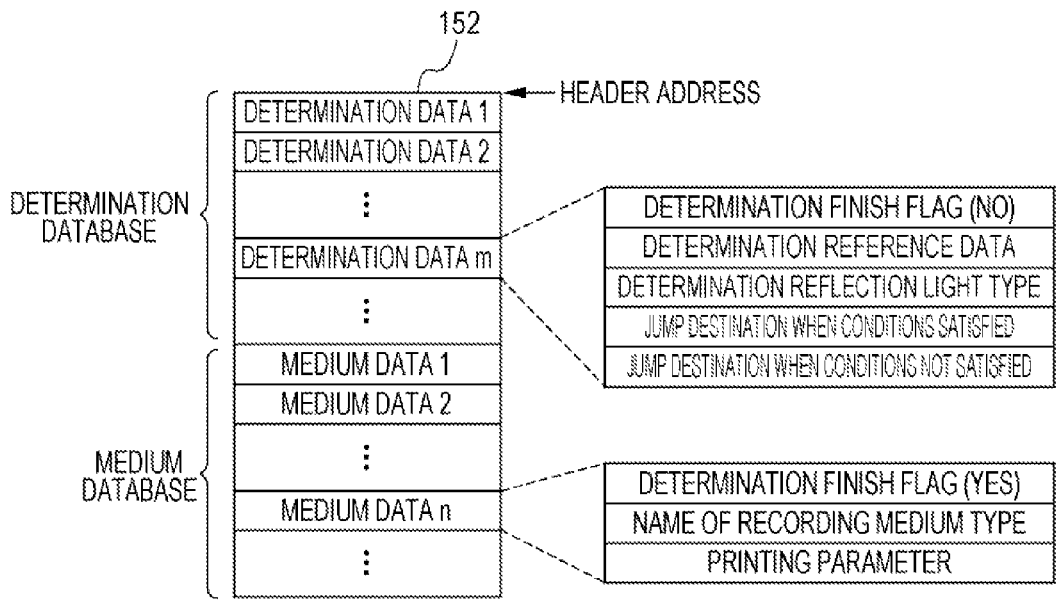

FIG. 7A is a diagram schematically showing a configuration of a controller for performing a recording medium determination process. FIG. 7B is a diagram showing an example of a database array in the controller. More specifically, FIG. 7A is a diagram showing a configuration example of a controller 150, and FIG. 7B is a diagram showing a data structure example of a determination database array provided in the controller 150. As shown in FIG. 7A, a CPU 151 that executes various processes, and a determination database array 152 as a reference data saving destination that the CPU 151 references in the determination process are provided in the controller 150. The reflectivity data Sr, Sg, and Sb for each color component of the regular reflection light output from the regular reflection light detecting device 120, and the reflectivity data Dr, Dg, Db of each color component of the diffused reflection light output from the diffused light detecting device 130 are input to the CPU 151. The CPU 151 executes the recording medium determination process using the reflectivity data thus provided and the determination database array 152.

The determination database array 152, as shown in FIG. 7B, includes a determination database formed from a plurality of sets of determination data groups, and a medium database formed from a plurality of medium data groups.

The determination database corresponds to the binary tree in FIG. 5 as a computer processing simple data structure, and is formed from a number of sets of determination data corresponding to the number of nodes in the binary tree. One set of determination data in the determination database includes information related to the type of reflection light data used in a branching decision at a node in the binary tree (determination reflection light type) and the threshold value thereof (determination reference data), and information related to a jump destination in the determination database array 152 for each of when branching conditions are satisfied and when not satisfied (a jump destination when conditions are satisfied and a jump destination when conditions are not satisfied). In addition, a flag indicating whether the determination process continues or finishes is further included. In the determination data, the flag is uniformly set to a value indicating "NO".

The medium database includes a number of sets of medium data corresponding to the number of types of recording medium registered in advance, and each item of medium data includes a unique title that discriminates each recording medium (recording medium type name), and the processing conditions when the recording medium is provided to the printing process, for example, transport conditions or parameters such as image density (printing parameters). In addition, a flag indicating whether the determination process continues or finishes is further included. In the medium data, the flag is uniformly set to a value that indicates "YES".

FIG. 8 is a flowchart showing one example of a recording medium determination process that is executed by the controller. Initially, the value of a pointer indicating a reference address in the determination database array is set to the header address of the determination database array (Step S101). Next, the determination data of the designated address is read from the determination database (Step S102).

Subsequently, the value of a determination finish flag from the read data is determined (Step S103). Since the flag in each item of determination data in the determination database is set to "NO", the determination result at this time is "NO", and Step S104 is executed next. That is, determination reference data from the determination database and the determination reflection light type are acquired (Steps S104, S105). Then, one item specified according to the determination reflection light type from the measured reflectivity data in the reflection light from the recording medium M is selected (Step S106), and the value thereof and the determination reference data acquired from the determination database are compared (Step S107).

Here, while in a case in which the condition of "(measurement data)<(reference data)" is satisfied (Yes in Step S107), the pointer is updated to the jump destination when conditions are satisfied indicated by the determination data (Step 109), in a case in which the conditions are not satisfied (NO in Step S107), the pointer is updated to the jump destination when conditions are not satisfied (Step S108). Thereafter, the database is newly read by returning to Step S102.

At this time, if the jump address designated by the pointer is in the determination database, the above process is repeated on the basis of the designated determination data. This indicates that the branching decision progresses one layer deeper in the binary tree. Meanwhile, if the jump destination designated by the pointer is in the medium database, the data subsequently read out is the medium data. In the medium data, since the determination finish flag is set to "YES", the determination in Step S103 proceeds to Step S110 by becoming "YES", and the process ends by acquiring the recording medium type name and the printing parameters from the medium data designated by the pointer. This indicates that the search along the binary tree arrives at a "leaf", and the type of recording medium corresponding to the leaf is obtained as the determination result.

In a printing apparatus or the like equipped with the determining device 100, it is possible to use the recording medium type name acquired as the determination results for notifying a user, for example, of the determination results. In addition, in a case in which the printing process to be executed and the recording medium do not match, it is possible to use applications such as performing a warning notification or pausing the printing process. In addition, it is possible to use the printing parameters read out from the medium database, for example, for achieving optimization of the processing conditions of the printing process.

Figure 9A:
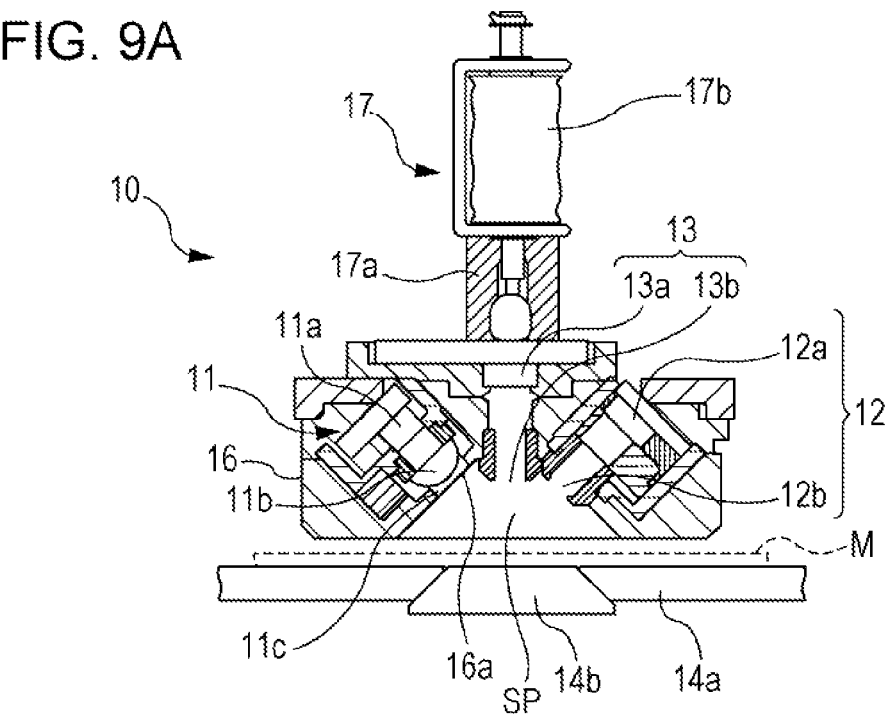
FIGS. 9A to 9C are lateral cross-sectional diagrams showing a more specific configuration of a determining device.
Figure 9B:
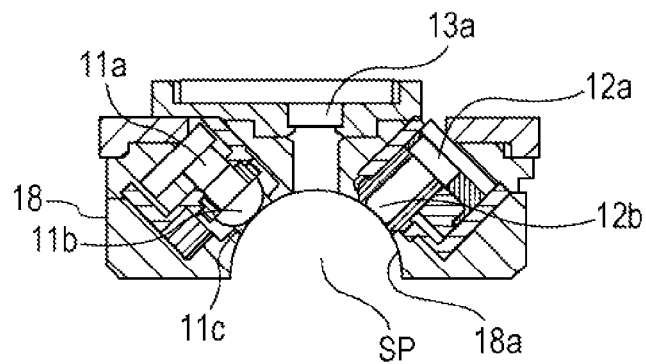
Figure 9C:
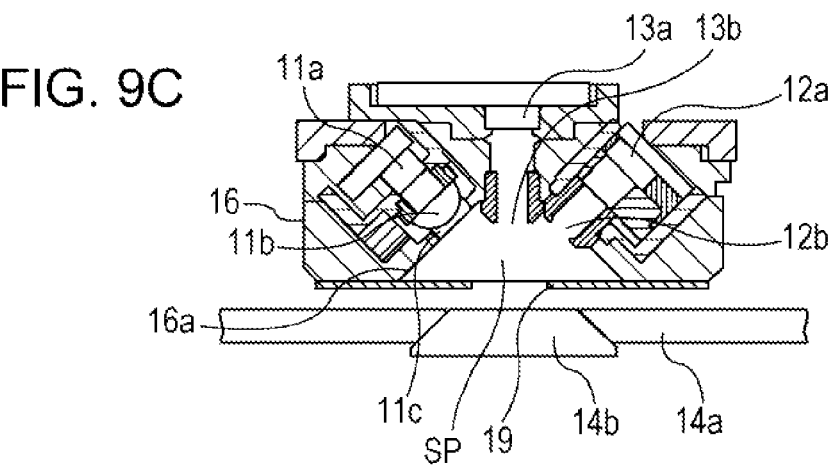

FIG. 9A is a lateral cross-sectional diagram showing a more specific configuration of a determining device. FIG. 9B is a lateral cross-sectional diagram showing a more specific configuration of a determining device. FIG. 9C is a lateral cross-sectional diagram showing a more specific configuration of a determining device. A light source unit 11, a regular reflection light receiving unit 12 and diffused light receiving unit 13 corresponding respectively to the light source device 110, the regular reflection light detecting device 120 and the diffused light detecting device 130 of the above-described determining device 100 are included in the determining device 10 shown in FIG. 9A, and these are accommodated in the housing 16 that is a cavity in which the interior having an opening in the lower surface functions as the measurement space SP. The housing 16 prevents disturbance due to stray light or the like by irradiation and reflection of light being performed in an internal cavity, while holding the positional relationship between each unit.

Although it is normally preferable that the inner wall surface 16a of the housing 16 that faces the measurement space SP be matte black, white or a mirror finish may also be used. Moreover, as shown in FIG. 9B, a housing 18 may be used in which an inner surface wall 18a has a semi-circular cross-sectional shape. In addition, as shown in FIG. 9C, an aperture diaphragm 19 may be provided on the lower surface of the housing 16 in order to prevent mixing of reflection light from the surface of the platen 14a other than the reference reflection plate 14b.

A platen 14a is arranged below the determining device 10, and the reference reflection plate 14b is fitted to a through hole opened in a part thereof. These correspond to the previously described platen 140 and reference reflection plate 141.

In addition, the housing 16 is held to freely move up and down by a housing elevating mechanism 17. That is, a lift arm 17a that extends upward is attached to the upper portion of the housing 16 and the lift arm 17a moves up and down accompanying the operation of an elevation driving portion 17b using, for example, a solenoid. Therefore, by operating the elevation driving portion 17b, the housing 16 moves to approach and separate with respect to the platen 14a by moving up and down. In a state in which the housing 16 is furthest lowered, the lower surface of the housing 16 comes into contact with the upper surface of the platen 14a, either directly or via the recording medium M arranged on the platen 14a. In so doing, it is possible to prevent outside light from infiltrating to the measurement space SP.

The light source unit 11 includes a white LED 11a with high color rendering properties that is an irradiation light source, a condenser lens 11b in which the irradiated light therefrom is collected, an emission diaphragm 11c that restricts the emission direction of the collected light. In addition, the regular reflection light receiving unit 12 includes a light sensor 12a that receives regular reflection light from the reference reflection plate 14b or the recording medium, and an entrance diaphragm 12b that restricts the incident light to the light sensor 12a. Similarly, the diffused reflection light receiving unit 13 includes a light sensor 13a that receives diffused reflection light from the reference reflection plate 14b or the recording medium, and an entrance diaphragm 13b that restricts the incident light to the light sensor 13a.

Figure 10:
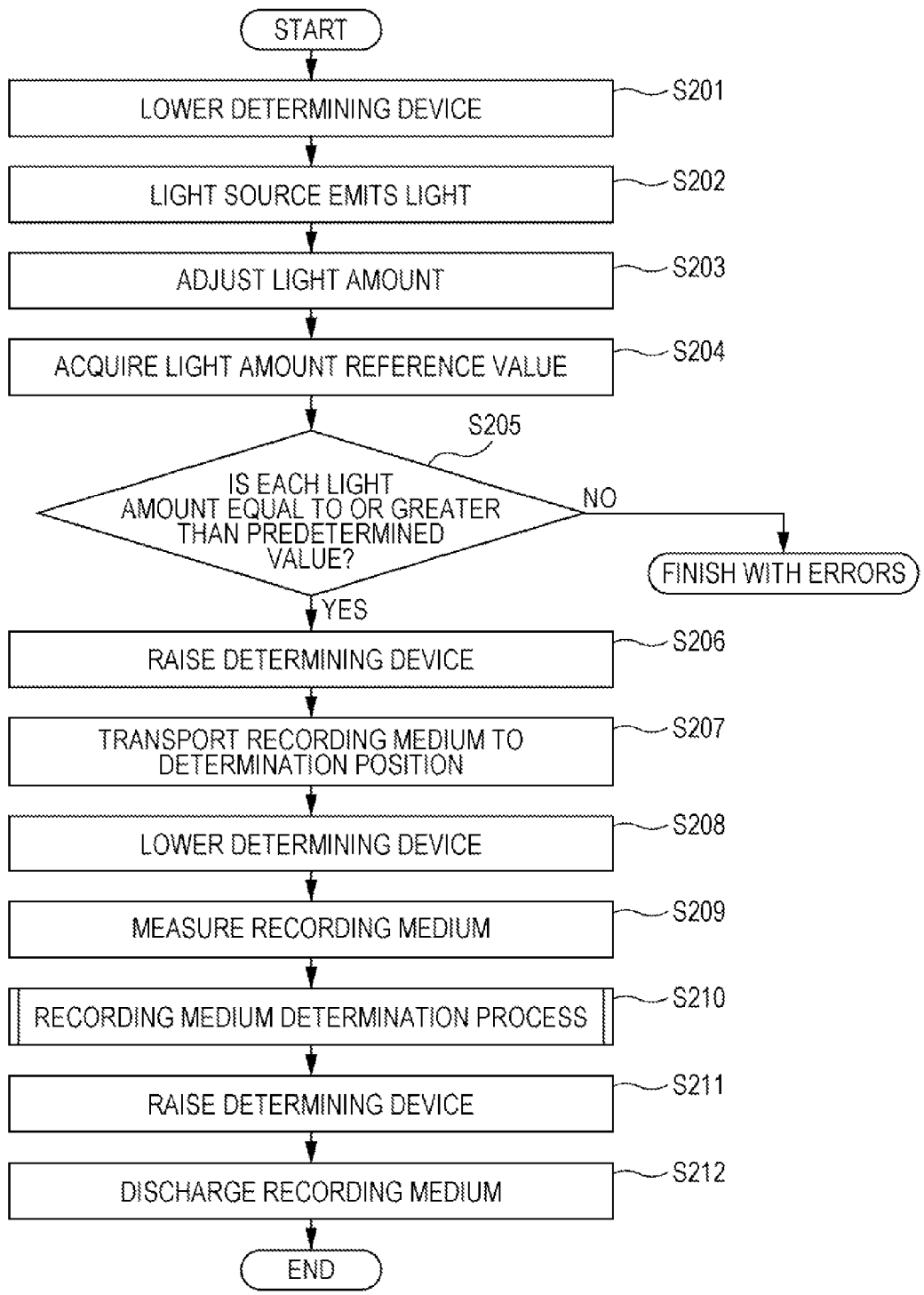
FIG. 10 is a flowchart showing a determination process operation including calibration.

FIG. 10 is a flowchart showing a determination process operation including calibration of the determining device. Firstly, before the recording medium is arranged on the platen 14a, the determining device 10 is lowered by the housing elevating mechanism 17, and the lower surface of the housing 16 enters a state of being in tight contact with the upper surface of the platen 14a (Step S201). In this state, the LED 11a that is an irradiation light source emits light, and light amount adjustment is performed such that the light amount is suitable and stable in the measurement (Step S202).

In this state, the regular reflection light and the diffused reflection light from the reference reflection plate 14b are received by the regular reflection light receiving unit 12 and the diffused reflection light receiving unit 13, and the received light amount is obtained for each of the RGB color components. The values thereof are acquired as reference values when the reflectivity of the recording medium is obtained (Step S204). By acquiring the reflection light from the reference reflection plate 14b as a reference value, it is possible to obtain stable determination results regardless of variations in the characteristics of the light source and light receiving portion, or changes therein over time. That is, acquisition of the reference values here has the meaning of calibration of the determining device. Then, the received light amount of each component is determined (Step S205), and when a predetermined value set in advance is not reached, since an abnormality of the determining device is suspected, the process finishes with an error.

If each received light amount is normal, the determining device 10 is temporarily separated from the surface of the platen 14a by being raised by the housing elevating mechanism 17 (Step S206), and the lower surface of the housing 16 enters a state of tight contact with the upper surface of the recording medium M by the determining device 10 being lowered again (Step S208) after the recording medium that is a determination target is transported to the determination position directly below the determining device 10 (Step S207). In this state, light is irradiated toward the surface of the recording medium M, and measurement of the regular reflection light and the diffused reflection light is performed (Step S209).

Then, although the recording medium determination process is performed on the basis of the measurement results (Step S210), the processing content is the same as shown in FIG. 8. When the type of recording medium is determined in this way, the determining device 10 is separated from the recording medium M by being raised (Step S211), the recording medium is discharged (Step S212) and the process ends.

Figure 11A:
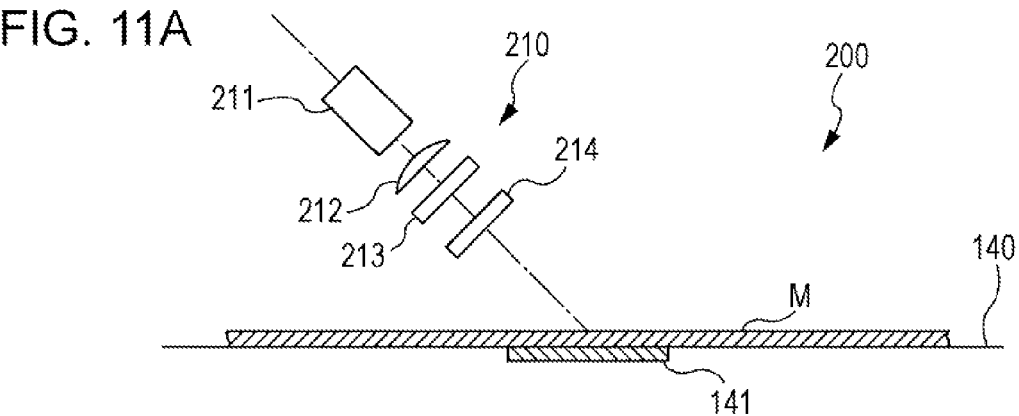
FIGS. 11A to 11C are diagrams showing another example of a specific configuration of a determining device according to an aspect of the invention.
Figure 11B:
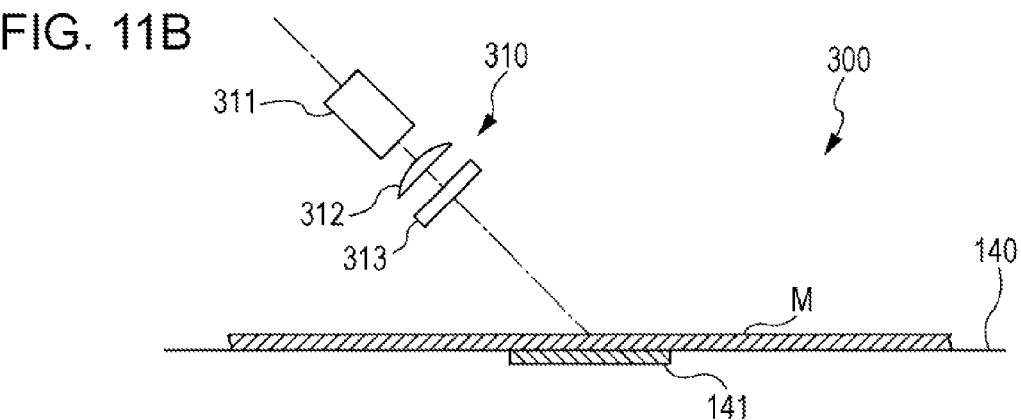
Figure 11C:
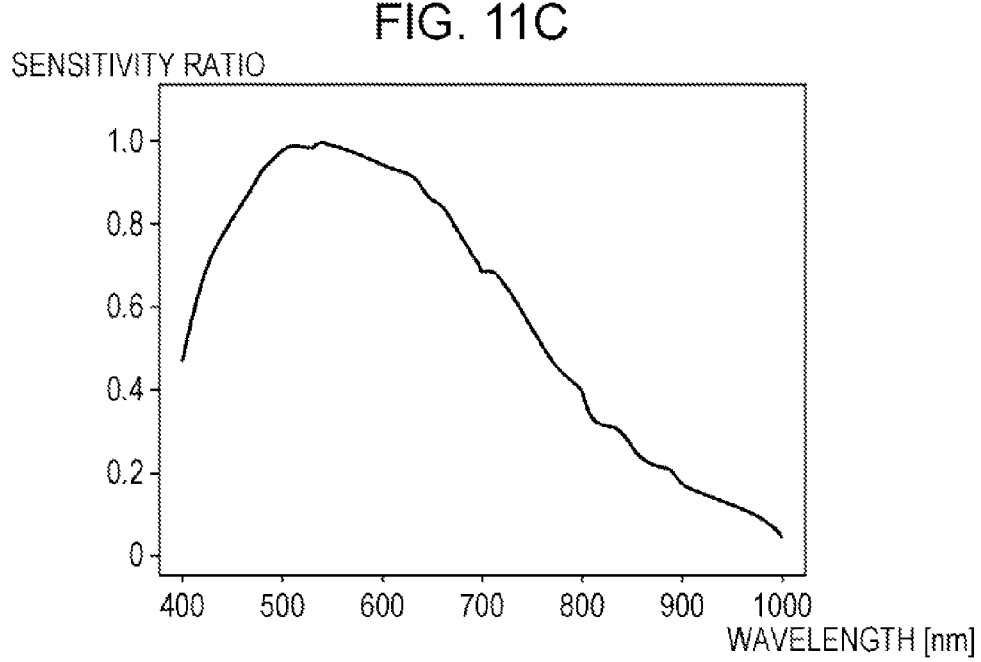

FIG. 11A is a diagram showing another example of a specific configuration of a determining device according to an aspect of the invention. FIG. 11B is a diagram showing another example of a specific configuration of a determining device according to an aspect of the invention. FIG. 11C is a graph showing the relationship between reflectivity and wavelength. In the determining device 200 of the configuration example shown in FIG. 11A, light from the light source device 210 is irradiated with respect to the recording medium M arranged on the platen 240 in which the reference reflection plate 241 is provided. The light source device 210 includes a light source portion 211 that emits light having a plurality of wavelengths, a light collecting portion 212 that collects the emitted light from the light source portion 211, a diaphragm portion 213 that regulates the radiation direction of the collected light, and a filter 214 through which only predetermined wavelength components from the light emitted through the diaphragm portion 213 selectively pass. The filter 214 is able to switch the wavelength of light that has passed through. That is, in the determining device 200, it is possible for the spectral distribution of light with which the recording medium M is irradiated to be changed by switching the filter 214.

In the determining device 300 of the configuration example shown in FIG. 11B, light from the light source device 310 is irradiated with respect to the recording medium M arranged on the platen 340 in which the reference reflection plate 341 is provided. The light source device 310 includes a light source portion 311 able to switch the wavelength of emitted light, a light collecting portion 312 that collects emitted light from the light source portion 311, and a diaphragm portion 313 that regulates the radiation direction of the collected light. It is possible to use a multicolor LED in which, for example, light emitting elements for each of the RGB colors are assembled in one package as the light source portion 311. That is, in the determining device 300, by the emission light components from the light source portion 311 being changed, it is possible for the spectral distribution of the light with which the recording medium M is irradiated to be changed.

Even in these configurations, the regular reflection light and the diffused reflection light are received for each wavelength component and the light amount detection results thereof are provided in the determination of the type of recording medium M. However, in contrast to the white light including a plurality of wavelength components at the same time being separated on the light receiving side by being irradiated on the recording medium M in the configuration example of FIGS. 3A to 3C, in these aspects, the wavelength components of light are already limited at the stage where the light is incident on the recording medium. Accordingly, as the light receiving portion receiving reflection light, in addition to being usable similarly to a light receiving portion having a light separating function as shown in FIGS. 3A to 4B, for example, it is possible to use a light receiving element having sensitivity with respect to a broad bandwidth of light, as shown in FIG. 11C. It is possible to use photoconductive cells and the like using a semiconductor sensor, a photomultiplier tube, and a photoconductive material such as cadmium sulfide, as such a light receiving element.

As an advantage due to the combination of light source portion able to switch the wavelength of incident light in this way and a light receiving element not having a color separating function, it is possible to individually set the incident light amount for each wavelength component. As shown in FIG. 1, the variance of the reflection light amount for each type of recording medium, in other words, the dynamic range in the light amount measurement differs greatly according to the wavelength of light. In the experiments by the inventors of the present application, as understood from FIG. 1, the long wavelength side in the visible range, in other words, the dynamic range in the red region becomes smaller. Therefore, for example, if the light intensity of the red color component of the incident light is made greater than the other color components, more high precision detection is possible by expanding the dynamic range of the red color component during measurement, and it is possible to increase the accuracy of the determination.

For example, in a recording medium such as a dark sheet in which the ground color is significantly distant from white, the short wavelength component included in the reflection light is reduced, and the red component and the infrared component are somewhat increased. Therefore, it is possible to more precisely detect the variance in the reflection characteristics for each type of recording medium and perform determination with high accuracy by expanding the dynamic range of the wavelength band.

If the reflection light amount for two or more wavelength components for each of the regular reflection light and the diffused reflection light is obtained, it is possible to determine the type of recording medium in the same manner as above by using the values thereof.

As above, in the embodiments of the determining device according to the aspects of the invention, the recording medium is irradiated with visible light, and the light amount of two or more wavelengths for each of the regular reflection light and the diffused reflection light are individually detected. Then, the detection results of the reflection light amount of the two or more wavelength components in the regular reflection light and two or more wavelength components in the diffused reflection light are used, and if the recording medium that is a determination target corresponds to any of the plurality of recording media for which the characteristics are known in advance is determined. Through doing so, it is possible to perform determination with only the total light amount of the regular reflection light and the diffused reflection light, and to determine with high accuracy more types of recording medium than in the related art that performs determination on the basis of the reflection light of fluorescent light excited by ultraviolet rays or the reflection light in the infrared region.

In the experiments by the inventors of the present application, a plurality of sheets for each of approximately 30 types recording medium totaling approximately 150 sheets were determined, and it was confirmed that the type was correctly determined with 100% probability.

In this determination method, either of the light source and the light receiving portion are able to be configured by a device that operates in the visible light range. Since numerous products are in practical use as such devices, by appropriately selecting from among these, it is possible to configure the determining device according to the intended use, cost or the like.

As described above, in this embodiment, the determining devices 10 and 100 correspond to the "recording medium determining device" of the aspects of the invention, the light source devices 110, 210, and 310 function as the "light irradiation portion" of the aspects of the present invention, and the regular reflection light detecting device 120 and the diffused light detecting device 130 respectively function as the "regular reflection light receiving portion" and the "diffused reflection light receiving portion" of the aspects of the invention. In addition, the controller 150 functions as the "determining portion" of the aspects of the invention, and the reference reflection plate 141 functions as the "reference reflection portion" of the aspects of the invention.

Moreover, the aspects of the invention are not limited to the above embodiments, and various modifications other than those described above are possible as long as not departing from the gist thereof. For example, in the above-described embodiments, a binary tree structured on the basis of reflectivity data acquired from known recording media, and the type thereof is determined from reflectivity data acquired with the recording medium that is a determination target. However, the essence of the aspects of the invention is performing determination using the light amount value of two or more wavelength components of each of the regular reflection light and the diffused reflection light, and there is no particular limit on the content of the calculation process for determination using these values.

In addition, although the reflection light is separated using an easily obtainable RGB color filter in the above embodiments, how many wavelength components the reflection light is separated into and which wavelength components are used are arbitrary and not limited to the above.

In addition, in the above-described determining device 10 and the recording medium determination process using the same, the determining device 10 comes into tight contact with the recording medium. Although this is to prevent infiltration of external light while allowing the optical axis of the regular reflection light from the light source device to the regular reflection light receiving device to be stabilized, the elevation device is preferably not included according to the usage. For example, a case in which there is no influence of external light by the determining device being arranged inside the case of a printing apparatus, corresponds thereto. In addition, in the case of a configuration that separates and contacts the determining device and the recording medium (or a support portion of the recording medium), the recording medium (or a support portion of the recording medium) may move.

In addition, in the above embodiments, although determination is performed by arranging the determining device above the recording medium arranged on a planar platen, the positional relationship of the recording medium and the determining device is not limited thereto, and, for example, the determining device may be provided laterally with respect to a recording medium transported in the vertical direction, and further, the determining device is preferably arranged on the lower surface side of the recording medium arranged horizontally. Moreover, in addition to a configuration in which the recording medium is arranged on a planar platen, the configuration which may detect reflection light by performing light irradiation with respect to the surface of a recording medium pressed by a guide member and the surface of a curved recording medium that is wound around a roller may be used.

In addition, stopping the recording medium during determination processing is not necessary, and the configuration which may detect reflection light by performing light irradiation with respect to the surface of a recording medium that is being transported and moved at a predetermined transport speed may be used.

The entire disclosure of Japanese Patent Application No. 2013-371, filed Jan. 7, 2013 and 2013-268710, filed Dec. 26, 2013 are expressly incorporated by reference herein.

What is claimed is:

1. A recording medium determining device comprising:
a light irradiating portion that irradiates a recording medium with visible light;
a regular reflection light receiving portion that receives regular reflection light regularly reflected by the recording medium irradiated with light from the light irradiating portion;
a diffused reflection light receiving portion that receives diffused reflection light diffusely reflected by the recording medium irradiated with light from the light irradiating portion; and a determining portion that determines the type of recording medium on the basis of each light amount of two or more visible light components with different wavelengths to one another among the light components received by the regular reflection light receiving portion and each light amount of two or more visible light components with different wavelengths to one another among the light components received by the diffused reflection light receiving portion.

2. The recording medium determining device according to claim 1, wherein the light irradiating portion irradiates the recording medium with light not substantially including ultraviolet rays.

3. The recording medium determining device according to claim 1, wherein at least one visible light component of the diffused reflection light used by the determining portion in the determination corresponds to blue or green.

4. The recording medium determining device according to claim 1, wherein at least one visible light component of the regular reflection light used by the determining portion in the determination corresponds to blue.

5. The recording medium determining device according to claim 1, wherein
the light irradiating portion irradiates the recording medium with light including two or more visible light components with wavelengths different to one another, and
the regular reflection light receiving portion and the diffused reflection light receiving portion obtain the light amount of each light component by separating incident light.

6. The recording medium determining device according to claim 1, wherein the light irradiating portion irradiates the recording medium by switching between two or more types of visible light with spectral distributions different to one another.

7. The recording medium determining device according to claim 1, further comprising a reference reflection portion irradiated with light from the light irradiating portion,
wherein the determining portion obtains a ratio of a light amount of regular reflection light from the recording medium and a light amount of regular reflection light from the reference reflection portion received by the regular reflection light receiving portion, and a ratio of a light amount of diffused reflection light from the recording medium and a light amount of diffused reflection light from the reference reflection portion received by the diffused reflection light receiving portion.

8. A recording medium determination method, comprising:
irradiating a recording medium with visible light;
receiving regular reflection light in which irradiated light is regularly reflected by the recording medium;
receiving diffused reflection light in which irradiated light is diffusely reflected by the recording medium; and
determining the type of recording medium on the basis of each light amount of two or more visible light components with wavelengths different to one another among the light components received in receiving the regular reflection light, and each light amount of two or more visible light components with wavelengths different to one another among the light components received in receiving the diffused reflection light.

* * * * *